(12) United States Patent
Dumont et al.

(10) Patent No.: US 12,133,963 B2
(45) Date of Patent: Nov. 5, 2024

(54) SYRINGE PACK AND METHOD OF PACKING A PREFILLED SYRINGE

(71) Applicant: HOFFMANN-LA ROCHE INC., Little Falls, NJ (US)

(72) Inventors: Richard Dumont, Basel (CH); Neil B. Cammish, Basel (CH); Markus Hemminger, Basel (CH); Cyrille Blintz, Basel (CH); Flora Felsovalyi, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 556 days.

(21) Appl. No.: 17/284,965

(22) PCT Filed: Oct. 14, 2019

(86) PCT No.: PCT/EP2019/077810
§ 371 (c)(1),
(2) Date: Apr. 13, 2021

(87) PCT Pub. No.: WO2020/078920
PCT Pub. Date: Apr. 23, 2020

(65) Prior Publication Data
US 2022/0133981 A1    May 5, 2022

(30) Foreign Application Priority Data
Oct. 15, 2018  (EP) ...................................... 18200428

(51) Int. Cl.
*A61M 5/00*    (2006.01)
*A61M 5/31*    (2006.01)
(Continued)

(52) U.S. Cl.
CPC .......... *A61M 5/002* (2013.01); *A61M 5/3137* (2013.01); *A61M 5/31505* (2013.01); *B65B 5/04* (2013.01); *A61M 2005/3139* (2013.01)

(58) Field of Classification Search
CPC ................ A61M 5/002; A61M 5/3137; A61M 5/31505; A61M 2005/3139; A61M 2005/31518; A61M 5/315
(Continued)

(56) References Cited

U.S. PATENT DOCUMENTS 5,339,955 A * 8/1994 Horan .................... A61B 50/33
206/370
6,228,324 B1 * 5/2001 Hasegawa ............... A61L 2/208
604/199
(Continued)

FOREIGN PATENT DOCUMENTS

CN    102795407 A    11/2012
CN    102883962 A    1/2013
(Continued)

OTHER PUBLICATIONS

Chinese Search Report issued in corresponding Chinese Patent Application No. 201980067848.7 dated Sep. 2, 2022.
(Continued)

*Primary Examiner* — Rafael A Ortiz
(74) *Attorney, Agent, or Firm* — MEDLER FERRO WOODHOUSE & MILLS PLLC

(57) ABSTRACT

A syringe pack with a prefilled syringe (1) and a packaging (2) comprises: a barrel part (11) with an orifice (113) at a proximal end and a flange portion (112) at a distal end; a plunger part (13) extending through the distal end of the barrel part (11) into the barrel part (11); a stopper (12) adjacent to a proximal end of the plunger part (13) and arranged inside the barrel part (11) such that a dosage
(Continued)

chamber (111) is formed inside the barrel part (11); and a drug substance arranged inside the dosage chamber (111), wherein the prefilled syringe (1) is arranged in the packaging (2) and the packaging (2) is configured to allow external sterilization of the prefilled syringe (1) arranged in the packaging (2). The packaging (2) comprises a containment part (21) having a fixing structure (211) which holds the barrel part (11) of the prefilled syringe (1) in a defined fix position; a constraining structure (23) which acts on the plunger part (13) of the prefilled syringe (1) to block a movement of the plunger part (13) of the prefilled syringe (1) in a distal direction; and a cover part (22) tightly closing the containment (21).

14 Claims, 7 Drawing Sheets

(51) Int. Cl.
*A61M 5/315* (2006.01)
*B65B 5/04* (2006.01)

(58) Field of Classification Search
USPC .......................................................... 206/364
See application file for complete search history.

(56) References Cited

U.S. PATENT DOCUMENTS

| | | | |
|---|---|---|---|
| 8,925,723 | B2 | 1/2015 | Folchini et al. |
| 11,000,643 | B2 | 5/2021 | Peruzzo |
| 2014/0078854 | A1* | 3/2014 | Head ...................... B01F 31/20 206/364 |
| 2014/0262883 | A1* | 9/2014 | Devouassoux ........ B65D 75/36 206/364 |
| 2014/0262884 | A1* | 9/2014 | Priebe .................... A61M 5/321 206/538 |
| 2018/0015217 | A1 | 1/2018 | Hasumi |
| 2018/0228971 | A1* | 8/2018 | Thorne .................... A61M 5/19 |
| 2020/0016322 | A1* | 1/2020 | Takahashi .............. A61K 8/737 |
| 2020/0023117 | A1* | 1/2020 | Maruyama ............. B65D 81/05 |
| 2020/0289742 | A1* | 9/2020 | Pfrang .................. A61J 7/0053 |
| 2021/0284406 | A1* | 9/2021 | McDonald ............ A61M 5/002 |

FOREIGN PATENT DOCUMENTS

| | | |
|---|---|---|
| CN | 103562088 A | 2/2014 |
| CN | 205574652 U | 9/2016 |
| JP | H08-57046 A | 3/1996 |
| JP | 2014-162532 A | 9/2014 |
| WO | 2012056265 A1 | 5/2012 |
| WO | 2018/181531 A1 | 10/2018 |

OTHER PUBLICATIONS

Chinese Office Action issued in corresponding Chinese Patent Application No. 201980067848.7 dated Sep. 2, 2022.
Notice of Reasons for Rejection issued Aug. 22, 2023 in Japanese Patent No. 2021-520188.
International Search Report and Written Opinion issued Dec. 10, 2019, in corresponding International Patent Application No. PCT/EP2019/077810.

* cited by examiner

SYRINGE PACK AND METHOD OF PACKING A PREFILLED SYRINGE

TECHNICAL FIELD

The present invention relates to a syringe pack according to the preamble of independent claim 1 and more particularly to a method of packing a prefilled syringe.

Syringe packs typically comprise one or more prefilled syringes (PFS) provided with a drug substance, and packaging. The PFS can have a cylindrical hollow barrel with an orifice at a proximal end and a flange portion at a distal end, a plunger rod extending through the distal end of the barrel into the latter, as well as a stopper adjacent to a proximal end of the plunger rod and arranged inside the barrel such that a dosage chamber is formed inside the barrel, which is filled with the drug substance. The PFS is arranged in the packaging and the packaging is configured to allow external sterilization of the PFS arranged in the packaging. Such syringe pack can be used in many applications for delivering the drug substance in a protected and easy administrable form.

BACKGROUND ART

Many pharmaceutical products (also referred to as drugs or drug substances) are processed and/or administered in liquid form wherein injecting the products often is preferred. More specifically, for subcutaneous, intramuscular, intradermal or intravitreal injection the pharmaceutical substances are often provided in prefilled syringes (PFS) wherein such syringes may have the needles staked-in or be equipped with an adapter for connecting a needle. In PFS, the drug substance is provided in the interior of a barrel of the syringe in a solution or other liquid form ready for being administered. Like this, the user receives a (quasi) ready-to-inject syringe without the requirement to prepare and fill the drug into the syringe, e.g. by transferring the drug from a vial into a disposable syringe.

Usually, prefilled syringes comprise a syringe barrel having an open end and a tip with an orifice essentially opposite to the open end, a rubber stopper, a plunger rod, an extended finger flange and a needle adapter cap with a rubber element. One common possibility for preparation of the PFS involves the following steps:

Assembling the needle adapter cap on the tip of the syringe barrel wherein the rubber element of the needle adapter cap tightly seals the orifice of the tip of the syringe barrel.

Sterilizing the assembly of syringe barrel and needle adapter cap. Thereby, the assembly often is exposed to a sterilizing agent at well-defined conditions, such as sterilant concentration, temperature, duration, relative humidity and/or pressure, allowing a complete sterilization of the assembly even in between the rubber element of the needle adapter cap and the tip of the syringe barrel. Frequently, ethylene oxide (EO) is used as sterilizing agent.

As an alternative to these two steps, the barrel and needle adapter cap can also be separately sterilized and assembly of both components can be performed in an aseptic environment.

After this first sterilization, a sterile drug substance is aseptically filled through the open end of the syringe barrel into an interior of the syringe barrel. Such aseptic filling typically is accomplished in cleanrooms in order to maintain sterility. Such cleanrooms are often classified, e.g., by the standards defined as "Sterile Drug Products Produced By Aseptic Processing" or "Manufacture of Sterile Medicinal Products" by Good Manufacturing Practice (GMP) for Active Pharmaceutical Ingredients (API) issued by the International Conference on Harmonisation Regulations. For many parenteral drugs such as ophthalmic drugs for intravitreal injection, the cleanrooms have to conform to the provisions for class A or clean area classification 100 of the GMP standards.

After aseptically filling the drug substance, the interior of the syringe barrel is sealed by advancing the sterile rubber stopper through the open end of the syringe barrel. This step typically is, again, accomplished aseptically in a cleanroom.

The sealed assembly is then typically moved out of the cleanroom and provided with the plunger rod and eventually with further elements such as, e.g., an extended finger flange and the like. It typically is packaged in a container such as a sterile barrier system.

For many products such as ophthalmic device combination products, after the PFS being assembled and packaged, the external surface of the syringe assembly must be sterilized. Thereby, in order to prevent the drug inside the syringe barrel to be affected, it is important to prevent that the sterilizing agent entering the interior of the syringe barrel. In particular, ingress of the sterilizing agent should be below the limits provided by health authority guidance and the International Organization for Standardization (ISO) requirements, and must not compromise the drug quality until the end of shelf life. Thereby, different sterilizing agents may have different limits. Thus, typically, during preparation of PFS two subsequent sterilizations are performed, a first one before filling the drug substance and a second final external surface sterilization once the PFS is completely assembled and packaged.

In the second final external surface sterilization often pressure is varied when providing the sterilizing agent. For example, when using vaporized hydrogen peroxide (VHP) as sterilizing agent, it may be desired to utilize a vacuum environment such as 4 mbar at 30° C. Such pressure variation, i.e. a pressure different from an ambient pressure, incurs risk that the stopper movements inside the barrel of the PFS to an inappropriate extent. For example, many stoppers are designed with plural circumferential sealing ribs. If the stopper moves to an extent exceeding a distance between the sealing ribs in external sterilization, the sterility of the interior of the barrel, i.e. the dosage chamber, may be compromised. Therefore, typically external sterilization is preferably performed with comparably low pressure variation.

However, there is a need for a device or method allowing comparably high pressure variation in the external sterilization of packaged prefilled syringes and, at the same time to guarantee that sterility inside the syringe is not impaired.

DISCLOSURE OF THE INVENTION

According to the invention this need is settled by a syringe pack as it is defined by the features of independent claim 1. Preferred embodiments are subject of the dependent claims.

In one aspect, the invention is a syringe pack with a prefilled syringe (PFS) and a packaging. The PFS comprises a barrel part with an orifice at a proximal end and a flange portion at a distal end; a plunger part extending through the distal end of the barrel part into the barrel part; a stopper adjacent to a proximal end of the plunger part and arranged inside the barrel part such that a dosage chamber is formed inside the barrel part; and a drug substance arranged inside the dosage chamber. The PFS is arranged in the packaging and the packaging is configured to allow external sterilization of the PFS arranged in the packaging. The packaging comprises a containment part having a fixing structure which holds the barrel part of the PFS in a defined fixed position; a constraining structure which acts on the plunger part of the prefilled syringe to block a movement of the plunger part of the PFS in a distal direction; and a cover part tightly closing the containment part.

The term "orifice" in connection with the barrel part relates to an outlet of the barrel part. In particular, the orifice can be integrally formed in the barrel part. The orifice is arranged to expel the drug substance once the plunger part is pushed into the barrel part such that a pressure in the dosage chamber is increased and the drug substance is forced out of the orifice. It can have a spout with a fluid passage. In one embodiment, the orifice can be directly equipped with a needle. In particular, the needle can be fixed to the orifice such that the drug substance can be provided through the needle. In another embodiment, the orifice can be equipped with an adapter such as a Luer lock adapter or the like. The adapter can be arranged to be connected to a needle from exterior the barrel part.

The barrel part typically is more or less hollow. It can have a nominal fill volume of about 1.0 ml or less. It can be essentially cylindrical having a circular cross section. In many embodiments of a PFS the barrel part is made of glass or a thermoplastic polymer, such as a cycloolefin copolymer (COO) or a cycloolefin polymer (COP). A barrel part manufactured from such materials can ensure a desired robustness, inertness and low gas permeability. Therefore, it allows for a convenient handling and a long-term storage which can be preferred for many pharmaceutical or drug products.

The stopper can be an elastic sealing element tightly closing the hollow interior of the barrel part. It may be made of an inert and resiliently deformable material such as a natural rubber material, a synthetic rubber such as a thermoplastic elastomer, or silicone. In particular, it can be embodied to seal the dosage chamber in the interior of the barrel part containing fluid(s) or a solid and a fluid. Further, it can have a face oriented towards the liquid in the dosage chamber and a face orientated in the distal direction. The outer circumference of the stopper can correspond to the inner circumference of the barrel when fitted.

The stopper can be adjacent to the proximal end of the plunger part by loosely contacting the distal end or by being connected or fixed to the distal end. In particular, it may be equipped with a cavity or recess centrally positioned in order to receive a proximal portion of the plunger part in a centralized fashion. Further, the stopper can be equipped with plural circumferential ribs which are axially distant to each other. These ribs may allow for achieving tightness between the stopper and the barrel part and at the same time, provide friction which still allows moving the stopper upon pushing the plunger part. For example, when the barrel part of the PFS has a nominal fill volume of 1.0 ml or less, the stopper can be equipped with three ribs which may be spaced from each other in a range of by about 0.8 mm to about 1.7 mm, in a range of by about 1 mm to about 1.3 mm, in a range of by about 1.1 mm to about 1.2 mm, by about 1.15 mm or by about 1.5 mm. For large barrel parts, the distance between the ribs may be greater.

The overall span between the stopper sealing ribs can be in a range of about 2 mm to about 2.6 mm, in a range of about 2.1 mm to about 2.5 mm, in a range of about 2.2 mm to about 2.4 mm or about 2.3 mm. For large stoppers, the overall span between the sealing ribs may be greater.

The term "drug" as used herein relates to a therapeutically active agent, also commonly called active pharmaceutical ingredient (API), as well as to a combination or plurality of such therapeutically active substances. The term also encompasses diagnostic or imaging agents, like for example contrast agents such as MRI contrast agents, tracers such as PET tracers, and hormones, that need to be administered in liquid form to the patient.

The term "drug substance" as used herein relates to a drug as defined above formulated or reconstituted in a form that is suitable for administration to a patient. For example, besides the drug, a drug substance may additionally comprise an excipient and/or other auxiliary ingredients. A particularly preferred drug substance in the context of the invention is a drug solution, in particular a drug solution for injection.

Typically, the liquid inside the chamber of the syringe barrel is a drug substance. In case of a double chamber PFS one chamber may comprise the drug substance which has to be reconstituted for drug administration by a diluent which is contained in a second chamber. Alternatively the first and second chamber may contain two different drug substances which have to be mixed before drug administration. In particular, the syringe may house a specific dosage of the drug substance to be administered when being injected.

The term "drug product" as used herein relates to a finished end product comprising a drug substance or a plurality of drug substances. In particular, a drug product may be a ready to use product having the drug substance in an appropriate dosage and/or in an appropriate form for administration. For example, a drug product may include an administration device such as the PFS or the like.

In the context of the present invention, the term "proximal" is used to refer to a portion, an extremity or a component located closest to or a direction oriented towards a medicament or drug delivery site, when the PFS is in use. Thus, the proximal direction can be a direction towards the body or person to which the PFS is intended to be applied. For example, in embodiments of prefilled syringes having a needle intended to be pierced in the body or person and the plunger to be pushed for delivering a medicament through the needle, the proximal end of the PFS is established by the tip of the needle. The proximal direction can be the direction towards an end of the needle or a location of the skin of the patient penetrated by the needle upon delivery of the medicament or drug substance to the patient.

Conversely, the term "distal" is used to refer to a portion, an extremity or a component located furthest away from or a direction oriented away from a medicament delivery site. Thus, a distal direction can be a direction oriented away from a body or person to which the PFS would be applied. For example, in use, the distal end of the PFS can be the end of the plunger where a thumb of an operator is placed for forwarding the plunger in order to deliver the drug substance.

For allowing external sterilization of the PFS inside the packaging the containment part and/or the cover part can be permeable for a sterilization agent at certain conditions. In general, the term "sterilizing agent" as used herein relates to any liquid, gaseous or vaporized substance capable for externally or external sterilizing the PFS surface. For example, the sterilizing agent can be or comprise ethylene oxide (EO), hydrogen peroxide ($H_2O_2$), steam, vaporized hydrogen peroxide (VHP), vaporized peracetic acid (VPA), or nitrogen dioxide ($NO_2$). However, in particular, the containment and/or cover parts can be pervious for VHP at specific conditions such as at a temperature in a range of about 20° C. to about 40° C. or in a range of about 25° C. to about 35° C. or of about 30° C., and at a pressure in a range of about 2 millibar (mbar) to about 8 mbar or in a range of about 3 mbar to about 6 mbar or of about 4 mbar. The external sterilization can particularly be an external surface sterilization mentioned above.

The term "sterilize" as used herein relates to bringing a structure or element such as the PFS in a sterile state. Thereby, the term "sterile" relates to a maximum contamination rate allowing the PFS or another element to be used in an intended application. For example, it can relate to a state of the PFS conforming with the requirements and guidance according to the Standard ST67 of the American National Standards Institute (ANSI) and the Association for the Advancement of Medical Instrumentation (AAMI), i.e. to ANSI/AAMI ST67. More particularly, a sterility assurance level (SAL) value of $10^{-6}$ can be used for products to be labeled as sterile as specified in ANSI/AAMI ST67.

Thus, by means of the sterilizing agent or of the sterilization a situation free of any viable organisms can be achieved. In particular, sterilization can relate to a validated process used to render a product essentially free of viable organisms. In such a sterilization process, the increase of the microbiological death can be described by an exponential function. Therefore, the number of microorganisms which survive a sterilization process can be expressed in terms of probability.

The containment part can have a recess which is shaped in accordance with the PFS. It can be manufactured together with the cover part in a process similar as it is known from conventional blister packaging. Like this, the packaging can be manufactured at comparably low costs. Also, a manufacture in a sterile environment is efficiently possible that way.

By providing the package with the constraining structure blocking a movement of the plunger part of the PFS fixed in the containment part, the extent of movement of the plunger part during external sterilization can be minimized or a movement can even be prevented. Thereby, also movement of the stopper can accordingly be minimized or even prevented. Thus, sterility inside the PFS and particularly of the drug substance can securely be maintained during external sterilization of the PFS.

The plunger part typically has a generally elongated shape. It can be embodied with a rod-, bar-, stick-, post- or shaft-like portion which at a proximal end is designed to contact or to be connected to the stopper. It can be made of a thermoplastic polymer such as polypropylene. Such a plunger part can efficiently be manufactured, e.g. by injection moulding, and allows for providing appropriate characteristics. Preferably, the plunger part is distally ending in a thumb portion and the constraining structure of the packaging is configured to act on the thumb portion of the plunger part of the PFS to block the movement of the plunger part in the distal direction. In some embodiments the thumb or other portion of the plunger part can be equipped with a shape or feature to receive the constraining structure. In such embodiments, the constraining structure can be specifically configured or designed to act on this shape or feature of the plunger part.

Since the thumb portion typically has a larger diameter than the rest of the plunger part and often is equipped with a plane or slightly concave surface, it can form a portion of the plunger part which is comparably easy to grip, push or to apply a force on. Additionally, it typically is oriented such that it can conveniently be pushed towards the stopper of the PFS such that a pressure inside the dosage chamber can be increased. Thus, by acting on the thumb portion, the constraining structure can comparably easily be embodied in an efficient manner.

Preferably, the constraining structure of the packaging applies a force on the plunger part of the PFS such that the dosage chamber inside the barrel part of the PFS is compressed. In particular, the force applied to the plunger part may induce a slight movement of the plunger part towards the dosage chamber. Thereby, the plunger part pushes the stopper towards the dosage chamber, which compresses the dosage chamber. Compressing the dosage chamber particularly relates to a reduction of the volume of the dosage chamber by compressing gas, e.g. air located in a gap or in the headspace, or the drug substance inside the dosage chamber. By the constraining structure applying such force on the plunger part inducing compression of the dosage chamber, the position of the stopper may safely be fixed. Like this, movement of the stopper due to varying pressure conditions can be prevented or reduced.

Thereby, to cover dimensional tolerances of the packaging components, the force applied to the plunger part of the PFS by the constraining structure of the packaging preferably moves a proximal end side of the stopper of the PFS by about 0.2 mm to about 1 mm, preferably by about 0.3 mm to about 0.8 mm, more preferably by about 0.3 mm to about 0.7 mm and, particularly, by about 0.5 mm towards the orifice of the PFS. Pre-compressing of the dosage chamber by such a movement of the stopper allows for providing a sufficient fixing of the stopper during pressure variation occurring in external sterilization. Thus, movement of the stopper during external sterilization can sufficiently be reduced. For example, when the stopper is equipped with circumferential ribs about its periphery, which are spaced from each as mentioned above such pre-compression allows for providing a sufficient fixation or clamping of the plunger part and stopper.

Preferably, the constraining structure of the packaging comprises a rigid blocking element acting on the plunger part of the PFS. In particular, the rigid blocking element can act on the plunger part by abutting it and in particular, abutting its thumb portion.

Thereby, in one preferred embodiment, the rigid blocking element is integral with the containment part of the packaging. For example, the rigid blocking element can be formed by one or more walls or braces embodied in the containment part and positioned at a distal end of the plunger part. Such walls or braces may be inclined such that pushing the PFS into the containment part increasingly pushes the plunger part towards the dosing chamber. Such rigid blocking element formed in the containment part as one single unit or piece allows for efficiently manufacturing the constraining structure in a safe and robust manner. For example, such containment part with integral blocking element can be embodied by a molding, thermoforming or cold forming process.

In another preferred embodiment, the rigid blocking element is integral with the cover part of the packaging. Such rigid blocking element may comprise an indentation in the cover part which abuts or receives the plunger part and particularly a thumb portion of it. It can further comprise bonding strip indentations at both sides of the plunger part or the thumb portion thereof to prevent a sideward movement of the plunger part. Like this, the plunger part can efficiently and safely be held. The cover part having such rigid blocking element can efficiently be manufactured by embossing or the like.

Preferably, the constraining structure of the packaging comprises an insert acting on the plunger part of the PFS. Such an insert allows for conveniently embodying the constraining structure in the packaging in a manner suitable and adapted to the specific PFS or its plunger part.

Thereby, in one preferred embodiment, the insert of the constraining structure of the packaging is made of an elastic material, and is arranged between the thumb portion of the plunger part of the PFS and the containment part of the packaging. Such constraining structure allows for sophisticatedly apply an acting on the plunger part. In particular, such an insert of elastic material can be shaped such that it specifically suits to the plunger part or its thumb portion. It can be pressed or positioned into the containment such that it is located between the plunger part and the containment part. In particular, it can abut the plunger part at its distal end side.

In a similar other element, the insert of the constraining structure of the packaging is a fluid filled cushion, which is arranged between the thumb portion of the plunger part of the PFS and the containment part of the packaging. Thus, instead of an elastic material, this insert is made as a blown up or filled up cushion. The fluid used for filling the cushion can be a gas, a liquid, fluidic particles or a mixture thereof. Such cushion can be an efficiently manufacturable insert. Gas filled cushions can have the additional advantage that they can be designed in a way that the cushion expands when vacuum is applied. This may prevent or reduce stopper movement. After return to ambient pressure the cushion would shrink back to its initial size and the syringe content would not be pressurized anymore.

In another preferred embodiment, the insert of the constraining structure of the packaging is a pad having a series of slots and the thumb portion of the plunger part of the PFS is arranged in one slot of the series of slots. Such a pad can be designed to be located below the PFS, the plunger part or the thumb portion thereof. The slots can be aligned with an edge of the thumb portion such that the edge can be accommodated in one of the slots. The pad can be made of a material particularly suitable for holding the plunger part. For example, compared to the containment part, the pad can be made of a more robust or rigid material and/or manufactured to a higher precision.

In particular, the PFS can be appropriately pre-compressed by applying a proximal force onto the thumb portion such that the dosage chamber is compressed and then arranged in the containment part equipped with the pad such the thumb portion of the rod portion is arranged in and held by the slot it is accommodated in. Such slots also allow blocking a movement of the plunger part in both directions, i.e. a distal and a proximal direction.

For allowing a convenient and efficient pre-compression of the PFS, the pad of the constraining structure of the packaging comprises a series of teeth and one slot of the series of slots is formed between each two neighboring teeth of the series of teeth. Such a toothed pad allows for proximal movement of the rod portion when the PFS is arranged in the containment part such that the PFS can be conveniently pre-compressed.

Preferably, the constraining structure of the packaging comprises a series of slots integral with the containment part of the packaging and the thumb portion of the plunger part of the PFS is arranged in one slot of the series of slots. Such series of slots may have the similar effects as the slots of the pad mentioned above. However, by being integrally formed a particularly efficient manufacture of the syringe pack can be achieved.

Similarly, the constraining structure of the packaging preferably comprises a rib integral with the containment part of the packaging and abutting the thumb portion of the plunger part of the PFS.

Preferably, the constraining structure of the packaging comprises a containment holder and a plunger press, wherein the containment part is held in the containment holder and the plunger press acts on the thumb portion of the plunger part of the PFS via the containment part. Such a constraining structure being external of the containment part and the cover part allows for efficiently encase the PFS in the containment part and the cover part, and subsequently to fix the plunger part in order to prevent its movement during external sterilization.

Thereby, the containment holder of the constraining structure of the packaging preferably comprises a base plate equipped with the containment holder and the plunger press. This allows for efficiently embodying and handling the syringe pack.

Also, the plunger press of the of the constraining structure of the packaging preferably comprises a spring element tensioned such that a force is applied to the containment part and transferred to the thumb portion of the plunger part of the PFS. Such spring element allows for appropriately pre-compressing the PFS, i.e. pre-compressing the dosage chamber of the PFS, when the PFS is already arranged in the containment part. The plunger press can avoid that the syringe content, i.e. the drug substance and eventually some air or gas, is still pressurized after final sterilization.

In another aspect, the invention is a method of packing a PFS. The method comprises the steps of (i) obtaining the PFS having a barrel part with an orifice at a proximal end and a flange portion at a distal end, a plunger part extending through the distal end of the barrel part into the barrel part, and a stopper adjacent to a proximal end of the plunger part and arranged inside the barrel part such that a dosage chamber is formed inside the barrel part in which a drug substance is arranged; (ii) obtaining a packaging configured to allow external sterilization through the packaging; (iii) providing the packaging with a containment part having a fixing structure, a constraining structure and a cover part; (iv) arranging the PFS in the containment part of the packaging such that the fixing structure holds the barrel part of the PFS in a defined fixed position and such that the constraining structure acts on the plunger part of the PFS to block a movement of the plunger part of the PFS in a distal direction; and (v) tightly closing the containment part of the packaging with the cover part.

Thereby, arranging the PFS in the containment part of the packaging preferably comprises applying a force on the plunger part of the PFS such that the dosage chamber inside the barrel part of the PFS is compressed.

Such method allows for efficiently embodying the syringe pack according to the invention or its preferred embodiments described above and thereby achieving the effects and benefits described above.

BRIEF DESCRIPTION OF THE DRAWINGS

The syringe pack according to the invention and the method of packing a prefilled syringe according to the invention are described in more detail herein below by way of exemplary embodiments and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
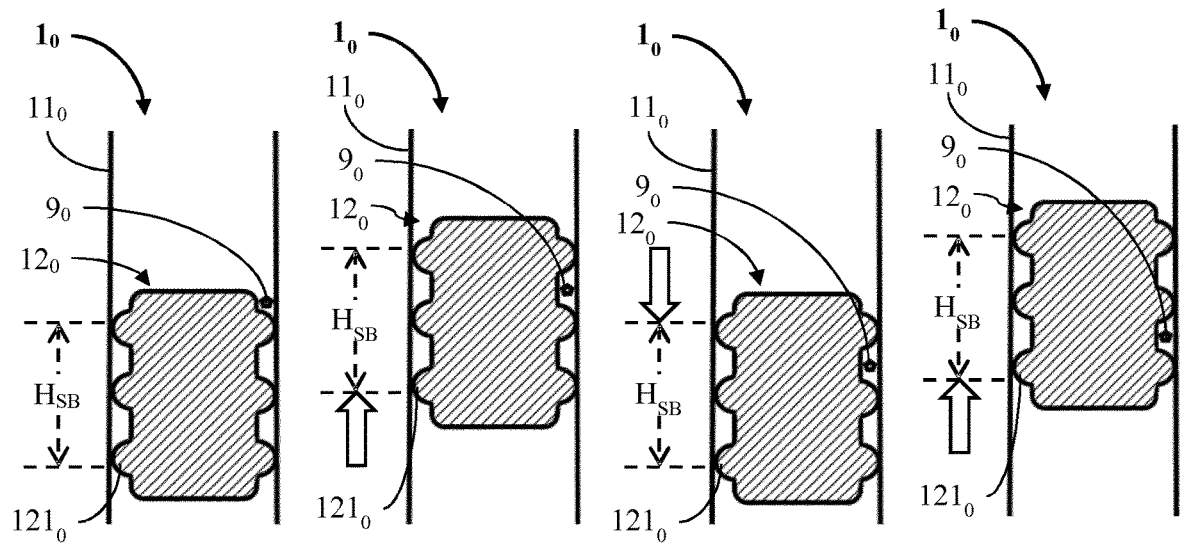
FIG. 1 shows a schematic view of contamination problems involved with a stopper moving due to varying pressure during external sterilization.

FIG. 1 shows four situations of a prefilled syringe $1_0$ (PFS) within an external sterilization process. The PFS $1_0$ has a glass barrel $11_0$ in which a stopper $12_0$ is positioned. The stopper $12_0$ has three axially spaced sealing ribs $121_0$ completely extending about the stopper $12_0$. The distance between the uppermost and lowermost sealing rib $121_0$ defines a span $H_{SB}$ which can e.g. be 2.3 mm. The stopper $12_0$ tightens the barrel $11_0$ into an upper portion and a lower portion. The upper portion can, e.g., be provided with a plunger (not visible in FIG. 1) to facilitate a movement of the stopper $12_0$ for activating the PFS $1_0$. The lower portion can form a dosage chamber in which a drug substance is arranged.

In the left-hand illustration, the PFS $1_0$ is depicted before or in the beginning of the external sterilization. Thereby, it can be seen that since the upper portion of the barrel $11_0$ is not tightly sealed a contaminant $9_0$ can travel to above the stopper $12_0$. As can be seen in the second illustration from the left, when the pressure is reduced around the PFS $1_0$, e.g. to efficiently apply vaporized hydrogen peroxide (VHP) for sterilization, the pressure inside the dosage chamber and in the headspace of the stopper $12_0$ is higher than above the stopper $12_0$. As indicated by the wide arrow, this forces the stopper $12_0$ to move upwardly. Thereby, the contaminant $9_0$ may get between the top and middle sealing ribs $121_0$ of the stopper $12_0$.

As can be seen in the second illustration from the right, when the pressure is raised again around the PFS $1_0$ to the original atmospheric pressure, the stopper $12_0$ is moved back downwardly to its original position as indicated by the wide arrow. In a next sterilization step shown in the right-hand illustration, the pressure around the PFS $1_0$ is lowered again, e.g. to a vacuum pressure of about 4 mbar, and the stopper $12_0$ is upwardly moved again. Thereby, the contaminant $9_0$ gets between the lower and the middle sealing rib $121_0$ of the stopper $12_0$.

Continuing such cyclic pressure drop and raise, which is beneficial for an efficient external sterilization by means of VHP, bears a substantial risk that contaminants $9_0$ end up inside the dosage chamber and, thus, in the drug substance. However, such risk has to be eliminated which can be done by the syringe pack according to the invention and, for example, the embodiments thereof described below.

Figure 2:
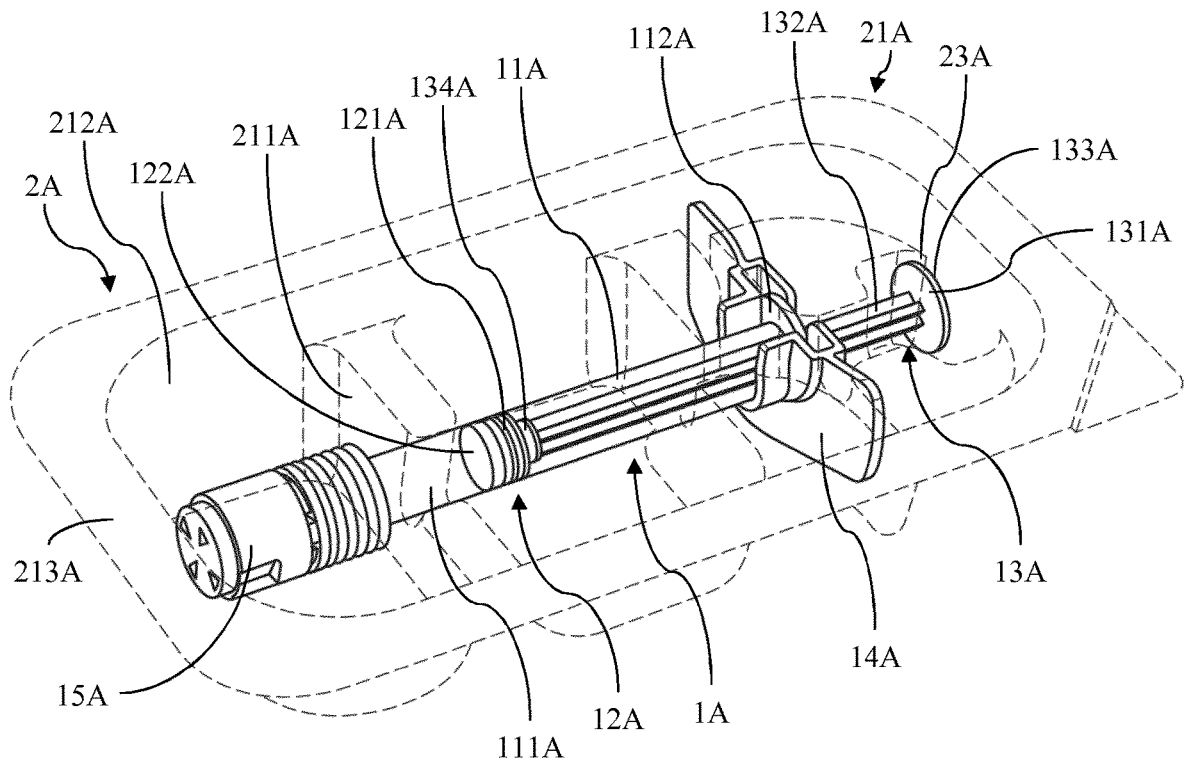
FIG. 2 shows a perspective view of a first embodiment of a syringe pack according to the invention.

In FIG. 2 a first embodiment of a syringe pack according to the invention is shown. The syringe pack comprises a prefilled syringe (PFS) 1A and a packaging 2A. The PFS 1A has a barrel 11A as barrel part, a plunger 13A as plunger part, a stopper 12A, a tip cap 15A and an extended finger flange 14A. The barrel 11A is essentially cylindrically shaped and made of glass. It has an orifice at a proximal end, a flange portion 112A at a distal end and a dosage chamber 111A in its interior. At the distal end the interior of the barrel 11A is completely open.

The stopper 12A has a cylindrical body about which circumferential sealing ribs 121A extend. The sealing ribs 121A are spaced from each other along an axis of the stopper 12A. The stopper 12A is advanced through the open distal end of the barrel 11A such that it is positioned in the interior of the barrel 11A. Thereby, a proximal front face 122A of the stopper 12A limits the dosage chamber 111A of the barrel 11A. More specifically, the dosage chamber 111A of the barrel 11A extends between the proximal end of the barrel 11A or its orifice and the front face 122A of the stopper 12A. Inside the dosage chamber 111A a drug substance is arranged.

The plunger 13A is embodied with a rod portion 132A, a thumb portion 131A forming a proximal end 133A and a distal end 134A. The thumb portion 131A has an enlarged diameter and is shaped to accommodate a thumb of a user of the PFS 1A. The rod portion 132A extends through the open distal end of the barrel 11A such that the distal end 134A contacts the stopper 12A inside the barrel 11A and the thumb portion 131A is outside the barrel 12A. In particular, the distal end 134A of the plunger 13A is connected to the stopper 12A such that any axial movement of the plunger 13A moves the stopper 12A as well.

The tip cap 15A is mounted to the orifice of the barrel 11A. Thereby, it covers a tip or spout of the barrel 11A which forms the orifice. The tip cap 15A is embodied to tightly and safely close the orifice and to protect the orifice. The extended finger flange 14A is clipped on the flange portion 112A of the barrel 11A. In use of the PFS 1A, it allows for receiving fingers of a hand of the user such that a counter pressure can be generated opposite to a pressure applied to the thumb portion 131A.

The PFS 1A is arranged in the packaging 2A. The packaging 2A is configured to allow external sterilization of the PFS 1A inside the packaging 2A. Thereby, the packaging 2A comprises a containment 21A as containment part and a cover as cover part which tightly closes the containment 21A. In FIG. 1, the cover is removed from the containment 21A such that an interior of the latter is visible.

In particular, the containment 21A is equipped with a chamber body 212A dimensioned to receive the PFS 1A and a horizontal skirt 213A limiting the chamber body 212A. The skirt 213A is sealed to the sheet-like cover in order to tightly close the packaging 2A. Inside the chamber body 212A the containment 21A has two transversal and one back fixing braces 211A as fixing structure. The fixing braces 211A have recesses shaped in correspondence to an outer form of the PFS 1A or of specific parts thereof. More specifically, the left most brace 211A has a central recess holding the barrel 11A at the dosage chamber 111A, the middle brace 211A has a central recess to hold the barrel 11A adjacent to the extended finger flange 14A and the back brace 211A has a recess to accommodate a section of the plunger 13A which extends out of the barrel 11A. Between the back brace 211A and the middle brace 211A there is a slot in which the extended finger flange 14A is positioned such that the barrel 11A is immovable along its axis.

The back brace 211A further forms a rigid section as constraining structure 23A abutting the thumb portion 131A of the plunger 13A. In particular, the rigid section acts on the proximal end side 133A of the plunger 13A. Thereby, the plunger 13A is forced into a distal direction along its axis such that the pressure in the dosage chamber 111A is raised. More specifically, the headspace of the PFS 1A is compressed by the rigid section of the back brace 211A acting on the thumb portion 131A of the plunger 13A. In that status, the PFS 1A is pre-compressed. A movement of the plunger 13A and the stopper 12A caused by a change of pressure in the containment 2A is thereby essentially reduced or even eliminated.

The packaging 2B is manufactured in a process similar to a conventional blister packaging process. In particular, the containment 21A is made from a thermoformed or cold formed plastic. The cover is made of a gas permeable but liquid tight synthetic foil such as a foil made of a high-density polyethylene material also known under the trademark Tyvek.

In order to avoid repetitive description the following applies: Unless specified to be different, the components or structures of the syringe pack shown in a specific Fig. are identical to the corresponding components and structures of the syringe pack of a previous Fig. More specifically, the components or structures of the syringe packs shown in the Figs. are provided with reference signs consisting of a numeral and a letter. Thereby, the numeral represents the particular component or structure and the letter represents the embodiment of the syringe pack according to the invention shown in the associated Fig. For example, the reference sign 1A represents the PFS (numeral 1) of the first embodiment of the syringe pack according to the invention (letter A). Thus, unless described to be different, the components and structures of a particular embodiment provided with reference signs are identical to the corresponding components and structures of a previous embodiment. For example, if the following description does not mention the plunger 13B of the second syringe pock shown in FIG. 3, it is identical to the plunger 13A of the syringe pack shown in FIG. 2.

Figure 3:
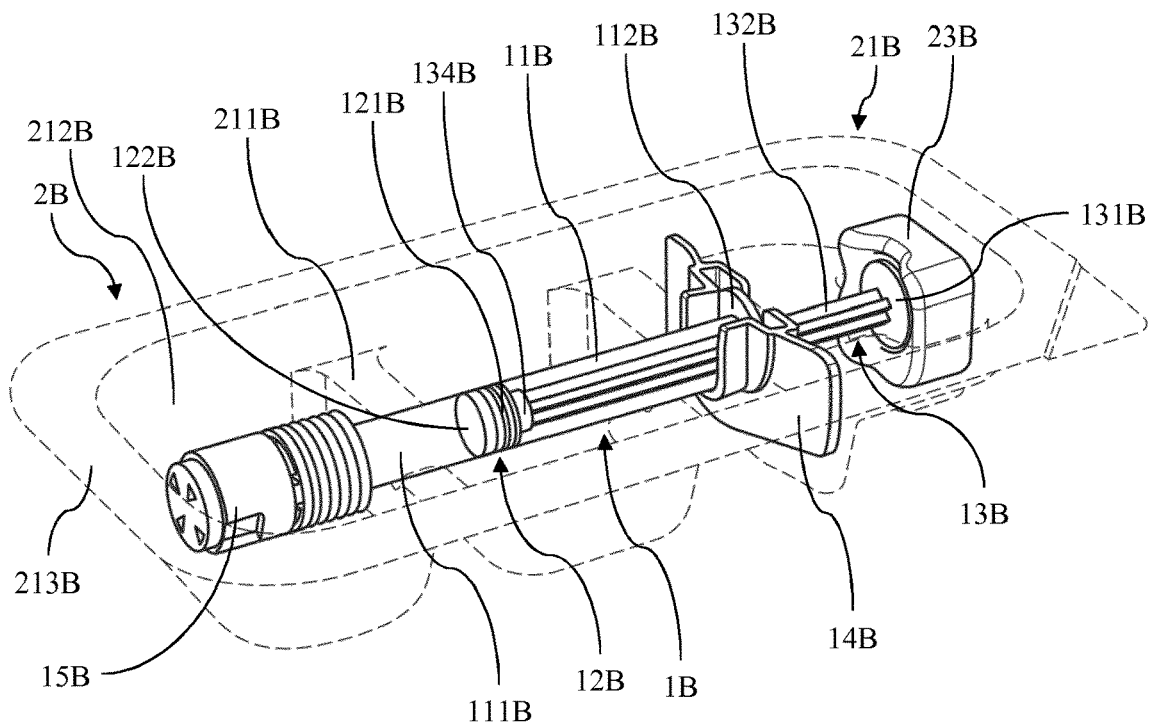
FIG. 3 shows a perspective view of a second embodiment of a syringe pack according to the invention.

FIG. 3 shows a second embodiment of a syringe pack according to the invention. The syringe pack comprises a PFS 1B and a packing 2B with a containment 21B and a cover. The PFS 1B and the cover of the packaging are embodied the same way as the PFS 1A and the cover of the first embodiment of the syringe pack described above in connection with FIG. 2. Also, the containment 2B of the packaging 2B is similar to the containment 2A of the first embodiment of the syringe pack described above in connection with FIG. 2.

However, a back fixing brace 211B of the containment 21B is shaped to receive a compressive insert 23B as constraining structure. The insert 23B is made of an elastic material. It is arranged between a thumb portion 131B of a plunger 13B of the PFS 1B and a right-hand end of the containment 21B. Thereby, it is compressed to a certain extent such that it acts on the plunger 13B of the PFS 1B by pushing it in a distal direction. Like this, a pressure in the dosage chamber 111B is raised and the headspace of the PFS 1B is compressed.

Figure 4:
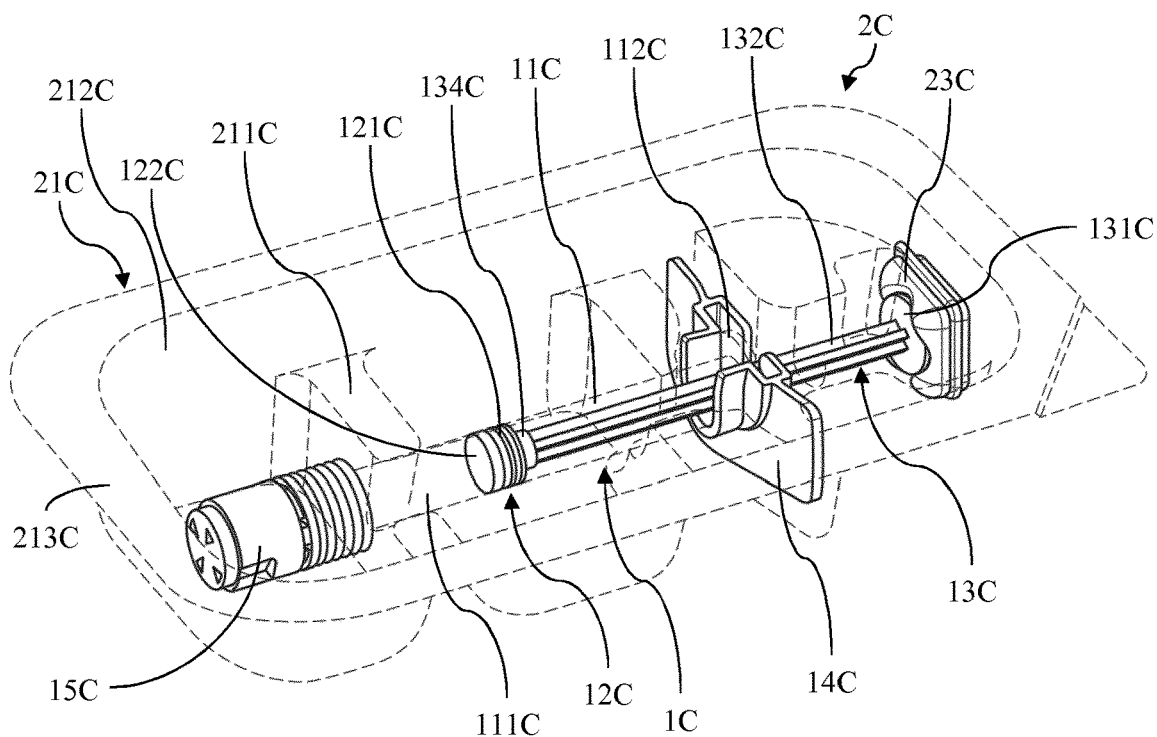
FIG. 4 shows a perspective view of a third embodiment of a syringe pack according to the invention.

In FIG. 4 a third embodiment of a syringe pack according to the invention is shown. It comprises a PFS 1C and a packaging 2C. The packaging 2C has a containment 21C with a back fixing brace 211C shaped to receive an air-filled cushion 23C as constraining structure. The insert 23C is made of two foils sealed at their borders and filled with air to a certain extent. It is positioned between a thumb portion 131C of a plunger 13C of the PFS 1C and a right-hand end of a containment 21C of the packaging 2C. Thereby, it is compressed to a certain extent such that it acts on the plunger 13C of the PFS 1B by pushing it in a distal direction. Like this, a pressure in the dosage chamber 111C is raised and the headspace of the PFS 1C is compressed.

Figure 5:
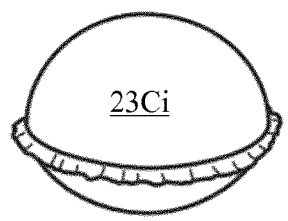
FIG. 5 shows a perspective view of an alternative fluid filled cushion to be used in the syringe pack of FIG. 4.
Figure 6:
FIG. 6 shows a perspective view of another alternative fluid filled cushion to be used in the syringe pack of FIG. 4.

FIG. 5 and FIG. 6 show two further embodiments of air filled cushions 23Ci, 23Cii to be used in the packaging 2C. In particular, cushion 23Ci has a circular general shape and cushion 23Cii a squared general shape.

Figure 7:
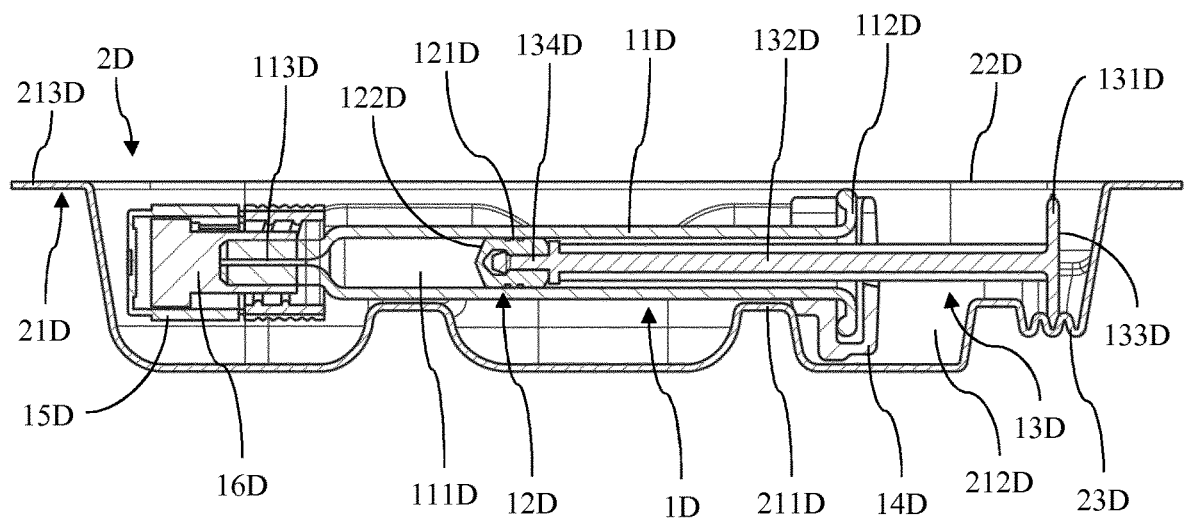
FIG. 7 shows a cross-sectional view of a fourth embodiment of a syringe pack according to the invention.

FIG. 7 shows a fourth embodiment of a syringe pack according to the invention. It comprises a PFS 1D and a packaging 2D. The packaging 2D has a containment 21D with an elevated bottom towards the right-hand end instead of a back fixing brace. The elevated bottom has a series of three transversal slots 23D as constraining structure integral with the containment 21D. In the middle slot 23D a thumb portion 131D of a plunger 13D of the PFS 1D is arranged. Like this, the plunger 13D is axially fixed such that an axial movement is prevented. In particular, the plunger 13D is fixed such that a pressure in a dosage chamber 111D of a barrel 11D of the PFS 1D is elevated and the headspace of the PFS 1D is compressed to a certain extent.

As can be seen in the cross-sectional view of FIG. 7, the orifice of the barrel 11D of the PFS 1D has a spout 113D with a central passage. The tip cap 15D is rigid and houses a sealing plug 16D, which tightly seals the central passage of the spout 113D. In particular, the spout 113D is closed by the sealing plug 16D which is protected by the tip cap 15D. Furthermore, it is depicted in FIG. 7 that the distal 134D of the plunger 13D is shaped as a plug which is received in a central cavity of the plunger 12D. Like this, the plunger 13D and the stopper 12D are firmly connected. The PFS of the other embodiments of syringe packs shown in the Figs. have an identical arrangement of spout, sealing plug, tip cap and plunger-stopper connection.

Figure 8:
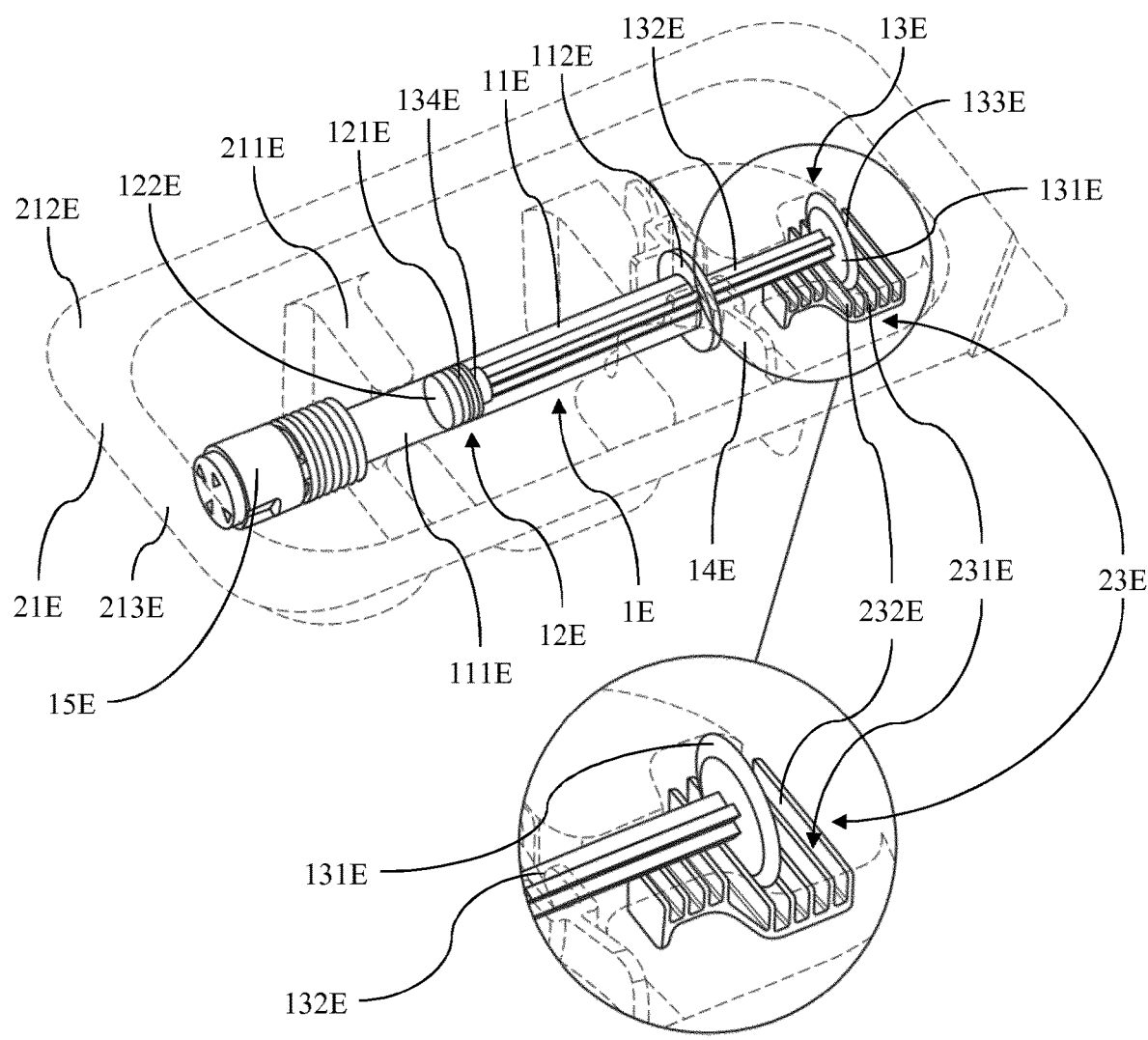
FIG. 8 shows a perspective view of a fifth embodiment of a syringe pack according to the invention and of a detailed section thereof.

In FIG. 8 a fifth embodiment of a syringe pack according to the invention is shown. It comprises a PFS 1E and a packaging 2E. The packaging 2E has a containment 21E with a back fixing brace 211E shaped to receive a pad 23E as constraining structure. The pad 23E is equipped with a series of transversal slots 231E separated by respective walls 232E. A thumb portion 131E of a plunger 13E of the PFS 1E is arranged in one of the slots 231E of the pad 23E. Like this, the plunger 13E is axially fixed by the two walls 232E neighboring the slot 231E such that an axial movement of the plunger 132E is prevented. In particular, the plunger 13E is fixed such that a pressure in a dosage chamber 111E of a barrel 11E of the PFS 1E is elevated and the headspace of the PFS 1E is compressed to a certain extent.

Figure 9:
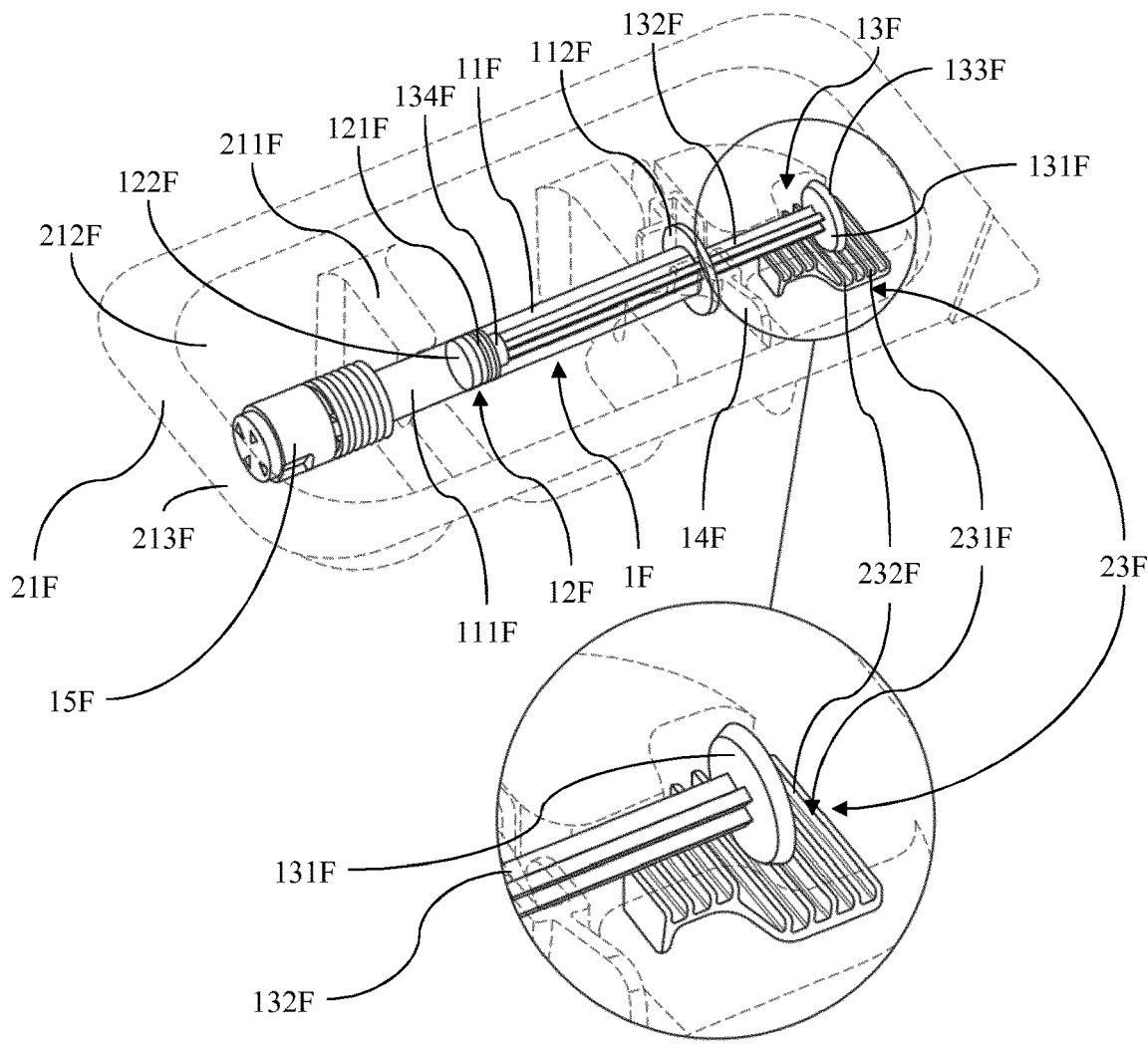
FIG. 9 shows a perspective view of a sixth embodiment of a syringe pack according to the invention and of a detailed section thereof.

FIG. 9 shows a sixth embodiment of a syringe pack according to the invention. It comprises a PFS 1F and a packaging 2F. The packaging 2F has a containment 21F with a back fixing brace 211F shaped to receive a pad 23F as constraining structure. The pad 23F is equipped with a series of transversal slots 231F separated by respective teeth 232F. A thumb portion 131F of a plunger 13F of the PFS 1F is arranged in one of the slots 231F of the pad 23F. Like this, the plunger 13F is axially fixed by the tooth 232F distally neighboring the slot 231F such that an axial movement of the plunger 132F in a distal direction is prevented. Due to provision of teeth 232F in the pad 23F, it is possible to advance the thumb portion 131F into a proximal direction but movement in the distal direction is blocked. Like this, the plunger 13F can be proximally forwarded until it is fixed in a position where a pressure in a dosage chamber 111F of a barrel 11F of the PFS 1F is elevated and the headspace of the PFS 1F is compressed to a certain extent.

Figure 10:
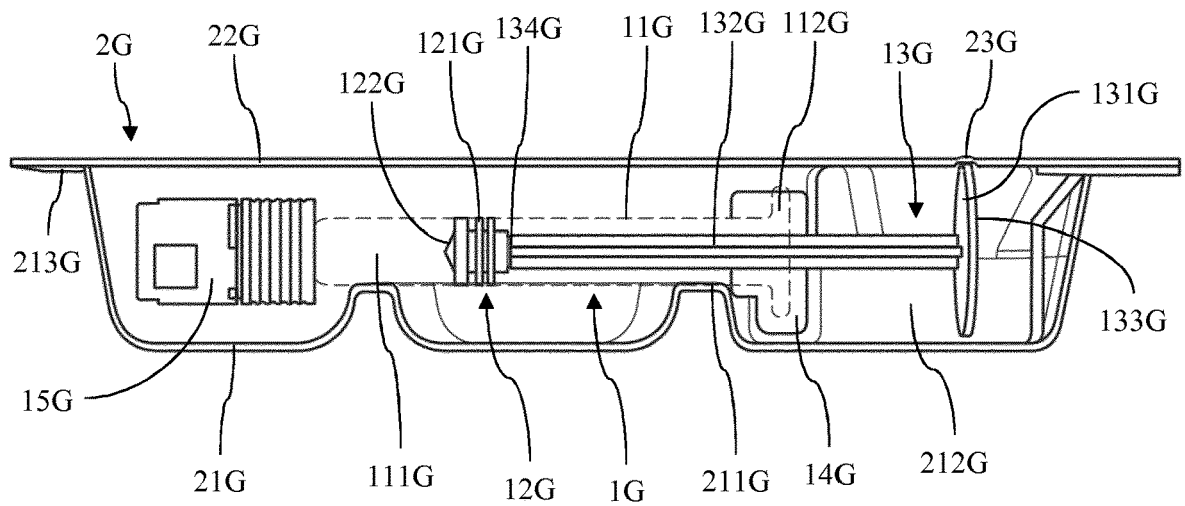
FIG. 10 shows a cross-sectional view of a seventh embodiment of a syringe pack according to the invention and of a detailed section thereof.
Figure 11:
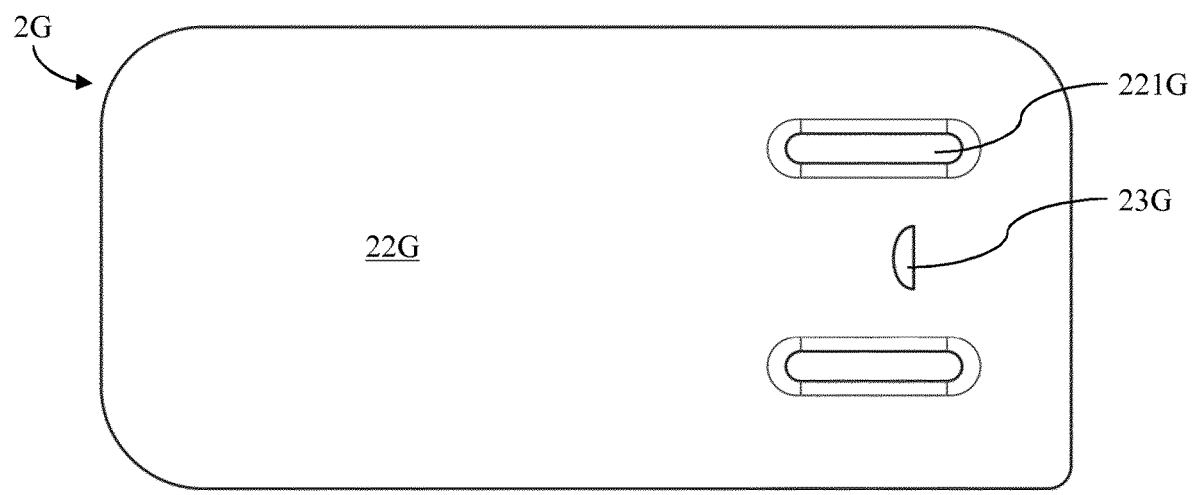
FIG. 11 shows a top view on the syringe pack of FIG. 10.

In FIG. 10 and FIG. 11 a seventh embodiment of a syringe pack according to the invention is shown. It comprises a PFS 1G and a packaging 2G. The packaging 2G has a containment 21G and a cover 22G. The containment 21G does not have a back fixing brace 211G. The cover 22G is equipped with a gripping bulge 23G above the top end of a thumb portion 131G of a plunger 13G of the PFS 1G as a rigid blocking element of a constraining structure integral with the cover part 22G. The bulge 23G receives the thumb portion 131G of the plunger 13G. Like this, the plunger 13G is axially fixed such that an axial movement is prevented. In particular, the plunger 13G is fixed when a pressure in a dosage chamber 111G of a barrel 11G of the PFS 1G is elevated and the headspace of the PFS 1G is compressed to a certain extent. The cover 22G is further provided with two parallel bonding strips 221G extending into a chamber body 212G of the containment 21G. The strips 221G are located at either side of the thumb portion 131G. Like this, the thumb portion 131G can be securely held.

Figure 12:
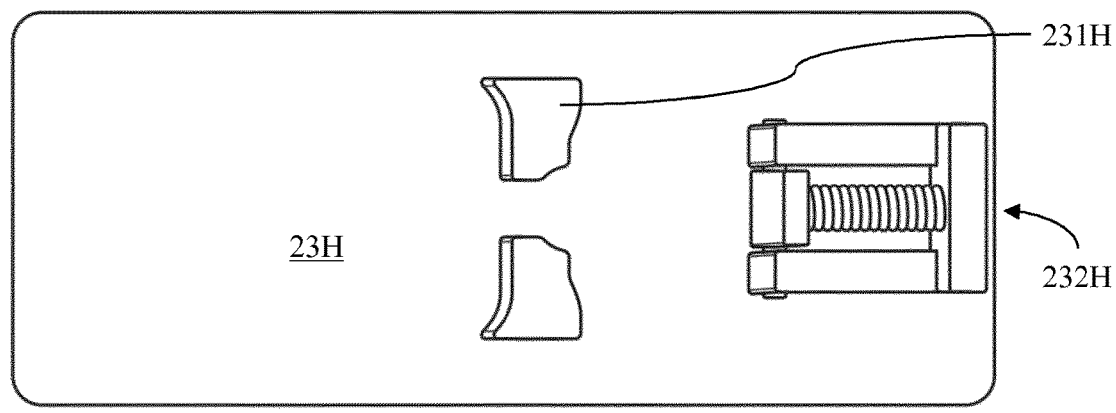
FIG. 12 shows a top view on an external constraining structure of an eighth embodiment of a syringe pack according to the invention.
Figure 13:
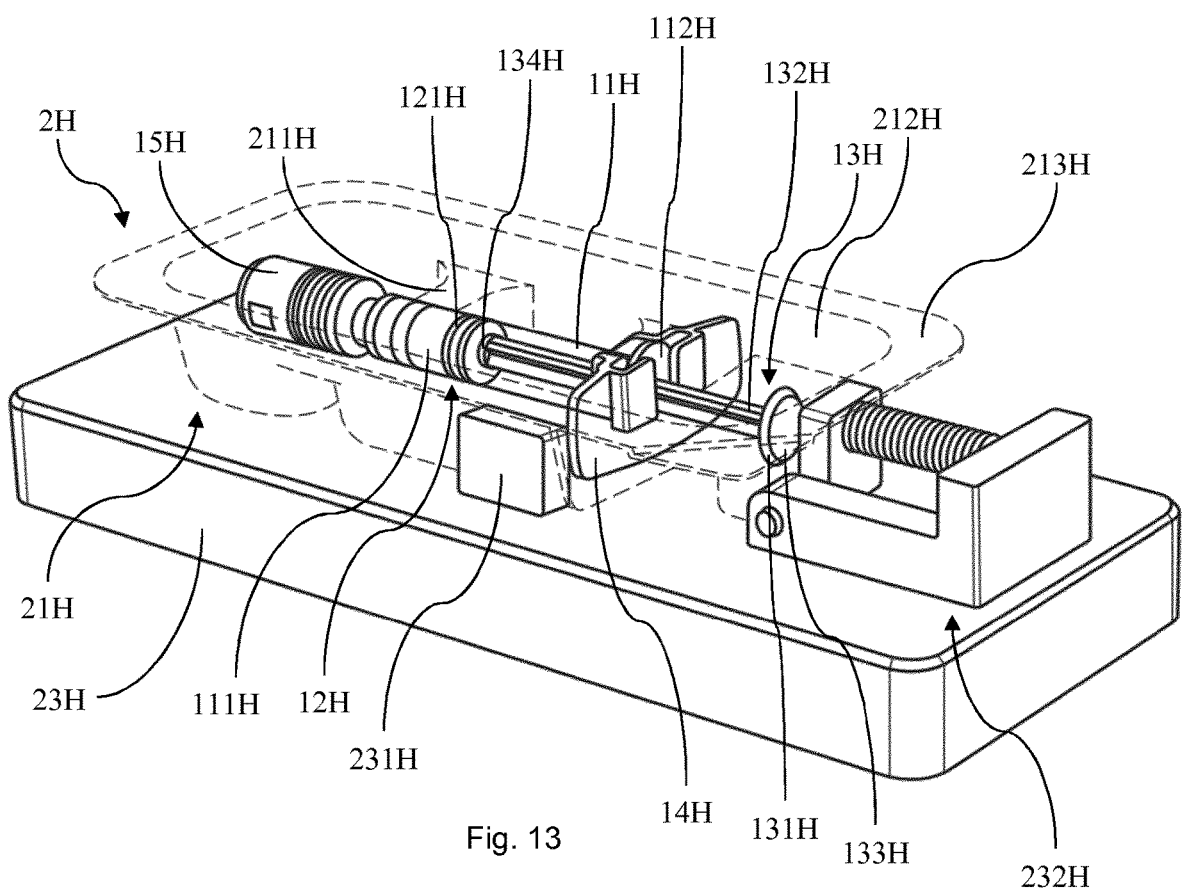
FIG. 13 shows a perspective view of the syringe pack of FIG. 12.

FIG. 12 and FIG. 13 show an eighth embodiment of a syringe pack according to the invention. It comprises a PFS 1H and a packaging 2H with a containment 21H and a cover. The containment 21H is not equipped with a back fixing brace 211H. The syringe pack further comprises an external constraining structure 23H with a base plate on which a containment holder 231H and a plunger press 232H are arranged. The containment holder 231H comprises two lateral blocks formed to receive the containment at one of its fixing braces 211H in between. Thereby, the containment 21H is held in the containment holder 231H. The plunger press 232H has a stamp part in a housing. A spring drives the stamp part towards a back side of the containment 21H such that it acts on a thumb portion 131H of a plunger 13H of the PFS 1H via the containment 21H. Like this, the plunger 13H is proximally forwarded and the headspace of the PFS 1H is compressed.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A syringe pack with a prefilled syringe and a packaging, the prefilled syringe comprising:
   a barrel part with an orifice at a proximal end and a flange portion at a distal end;
   a plunger part extending through the distal end of the barrel part into the barrel part;
   a stopper adjacent to a proximal end of the plunger part and arranged inside the barrel part such that a dosage chamber is formed inside the barrel part; and
   a drug substance arranged inside the dosage chamber,
   wherein the prefilled syringe is arranged in the packaging and the packaging is configured to allow external sterilization of the prefilled syringe arranged in the packaging, and
   wherein the packaging comprises:
      a containment part having a fixing structure which holds the barrel part of the prefilled syringe in a defined fixed position;
      a constraining structure which acts on the plunger part of the prefilled syringe to block a movement of the plunger part of the prefilled syringe in a distal direction; and
      a cover part tightly closing the containment part,
      wherein the constraining structure of the packaging applies a force on the plunger part of the prefilled syringe such that the force applied to the plunger part induces a slight movement of the plunger part towards the dosage chamber and the dosage chamber inside the barrel part of the prefilled syringe is compressed.

2. The syringe pack according to claim 1, wherein the plunger part is distally ending in a thumb portion and the constraining structure of the packaging is configured to act on the thumb portion of the plunger part of the prefilled syringe to block the movement of the plunger part in the distal direction.

3. The syringe pack according to claim 1, wherein the force applied to the plunger part of the prefilled syringe by the constraining structure of the packaging moves a proximal end side of the stopper of the prefilled syringe by about 0.2 mm to about 1 mm, preferably by about 0.3 mm to about 0.8 mm, more preferably by about 0.3 mm to about 0.7 mm and, particularly, by about 0.5 mm towards the orifice of the prefilled syringe.

4. The syringe pack according to claim 1, wherein the constraining structure of the packaging comprises a rigid blocking element acting on the plunger part of the prefilled syringe.

5. The syringe pack according to claim 4, wherein the rigid blocking element is integral with the containment part of the packaging.

6. The syringe pack according to claim 4, wherein the rigid blocking element is integral with the cover part of the packaging.

7. The syringe pack according to claim 1, wherein the constraining structure of the packaging comprises an insert acting on the plunger part of the prefilled syringe.

8. The syringe pack according to claim 7, wherein the insert of the constraining structure of the packaging is made of an elastic material and is arranged between a thumb portion of the plunger part of the prefilled syringe and the containment part of the packaging.

9. The syringe pack according to claim 7, wherein the insert of the constraining structure of the packaging is a fluid filled cushion and is arranged between a thumb portion of the plunger part of the prefilled syringe and the containment part of the packaging.

10. The syringe pack according to claim 1, wherein the constraining structure of the packaging comprises a rib integral with the containment part of the packaging and abutting a thumb portion of the plunger part of the prefilled syringe.

11. The syringe pack according to claim 1, wherein the constraining structure of the packaging comprises a containment holder and a plunger press, wherein the containment part is held in the containment holder and the plunger press acts on a thumb portion of the plunger part of the prefilled syringe via the containment part.

12. The syringe pack according to claim 11, wherein the containment holder of the constraining structure of the packaging comprises a base plate equipped with the containment holder and the plunger press.

13. The syringe pack according to claim 11, wherein the plunger press of the constraining structure of the packaging comprises a spring element tensioned such that a force is applied to the containment part and transferred to the thumb portion of the plunger part of the prefilled syringe.

14. The syringe pack according to claim 1, wherein the constraining structure is formed by a wall of the packaging that is inclined and configured such that pushing the prefilled syringe into the containment part increasingly pushes the plunger part towards the dosage chamber.

* * * * *